United States Patent [19]

Smith

[11] Patent Number: 5,267,481
[45] Date of Patent: Dec. 7, 1993

[54] ULTRA SOUND PROBE FOR CYLINDRICAL BODY HAVING REDUCED VERTICAL CLEARANCE

[75] Inventor: Thurman D. Smith, San Jose, Calif.

[73] Assignee: General Electric Company, San Jose, Calif.

[21] Appl. No.: 782,228

[22] Filed: Oct. 24, 1991

[51] Int. Cl.⁵ .................... G01N 29/10; G01N 29/24; G01N 29/26
[52] U.S. Cl. ........................ 73/623; 73/628; 73/641; 376/249
[58] Field of Search ............... 73/620, 622, 623, 628, 73/641; 376/249

[56] References Cited

U.S. PATENT DOCUMENTS

| 3,584,504 | 6/1971 | Proctor et al. | 73/623 |
|---|---|---|---|
| 4,642,215 | 10/1987 | Klinvex et al. | |
| 5,062,300 | 11/1991 | Vallee | 73/623 |
| 5,118,464 | 6/1992 | Richardson et al. | 73/623 |

FOREIGN PATENT DOCUMENTS

| 0333552A1 | 9/1989 | European Pat. Off. . |
|---|---|---|
| 0450868A2 | 10/1991 | European Pat. Off. . |
| 0493146A1 | 7/1992 | European Pat. Off. . |
| 1552897 | 9/1979 | United Kingdom . |

*Primary Examiner*—Hezron E. Williams
*Assistant Examiner*—Rose M. Finley
*Attorney, Agent, or Firm*—J. S. Beulick

[57] ABSTRACT

An especially designed probe carries preferably five transducers for the examination of a right circular cylinder flooded with water having limited vertical clearance from the point of required non destructive inspection. The probe includes a generally disc shaped body having a minimal vertical dimension and a radius slightly less than the radius of the right circular cylinder to be inspected. Insertion of the probe interior of the right circular cylinder occurs. At the periphery of the disc, there are disposed five interrogating acoustical transducers. These transducers are spaced from preselected staggered circumferential locations with respect to the right circular cylinder for examination of the water flooded cylinder with refracted rays. The respective transducers are disposed with disclosed angularities and spatial orientation from their point of intended inspection to satisfy Snell's law with respect to the diameter of the right circular cylinder being examined to enable all points on any given radius of the right circular cylinder to be acoustically interrogated. A process of interrogation is disclosed which includes mounting the disc on a rotatable shaft, elevating the disc on the shaft to an elevation having the point of required interrogation intersecting the disc. Upon rotation of the disc, each of the interrogating transducers rotates sequentially to the point of required acoustical interrogation for the desired non destructive acoustical interrogation of the right circular cylinder.

4 Claims, 5 Drawing Sheets

ULTRA SOUND PROBE FOR CYLINDRICAL BODY HAVING REDUCED VERTICAL CLEARANCE

This invention relates to so-called ultra sound probes. More specifically, an ultra sound probe is disclosed for use in inspecting a right circular steel structure at a point of required inspection where obstructions occur immediately adjacent the point of required inspection.

BACKGROUND OF THE INVENTION

Ultra sound probes are known. Specifically, such ultra sound probes have been used in the past to inspect right circular cylinders. In order to understand such inspection, first the parameters of a general inspection of an ordinary planar piece of material with acoustical transducers must be reviewed. Thereafter, the special problems in the examining a right circular cylinder will be set forth.

When a regular body (preferably a planar metallic body containing a weld) is examined, interrogation with five standard ultra sound transducers usually occurs. The ultra sound examination typically occurs from a planar surface on the suspect material disposed normally to a sound transducer. In understanding the direction of incidence of sound from interrogating transducers it is important to understand that in the acoustical interrogation here set forth, each transducer is both the transducer that sends interrogating and incident ultra sound as well as the receiver that receives the reflected ultra sound. It is the object of the ultra sound examination to provide inspection without destruction of the material—indicating either the physical limit of the material or the location of a possible defect. It will be understood, that the reflected signal received from the material being examined must be received in a direction that is parallel to the direction in which the signal was sent.

The ultra sound examinations here utilized occur in water. The preferred examination sites (the control rod drive housings and their supporting stub tubes) herein set forth are utilized with nuclear reactors which are typically flooded. Therefore, assuming that interrogation of the material being examined occurs at the above described angularities, problems of refraction in accordance with Snell's law occur.

Assuming that each transducer has its own interrogating direction, a standard array of transducers will include four transducers transmitting interrogating sound at 45° angles within the material being non destructively examined. Thus, for the complete examination of a structure having a normal surface of incidence, transducers send and receive interrogating ultra sound at angles within the material being examined upwardly at 45°, downward at 45°, left at 45°, right at 45°, and finally normal to the incident surface of the material being non destructively examined.

The interrogating sound that is analyzed in the non destructive examination is that component of ultra sound reflected back along the path of sound incidence. This being the case, reflection must occur from at least one—and as many as three surfaces of a corner cube array within the material. It is to be understood that such reflection can occur within a number of structures within the material including finished dimensions of the material, cracks, metallic interfaces, slag deposits in welds, and the like.

It is not the purposes of this patent application to set forth the entire field of ultra sound including sophisticated problems of diffraction limited acoustical apertures and the art of interpretation of the received ultra sound results. This will be left to those having skill in the art. Rather, it is the purpose of this document to set forth the general problems encountered in producing an interrogating and receiving array of transducers in the examination of a right circular cylinder where the clearance at the point of material interrogation is extremely limited.

Further, where the surface being examined is a right circular cylinder, the angle of incidence of the interrogating ultra sound rays must be constantly adjusted to account for the immediate curvature of the surface being examined and the interaction of diffraction in accordance with Snell's law. It is usually desirable to have the ultrasonic transducer aligned with respect to the right circular cylinder center line so that the ultra sound beam upon contact with the surface of incidence interrogates and returns to the receiving transducer with predictability. Where the sending and receiving paths are not carefully controlled, results of interrogation cannot be received.

In normal examinations of right circular cylinders, all five transducers are normally disposed in a vertical string and vertically stacked overlying one another. The interrogating transducers are given angularities of examination with respect to the string in accordance with the parameters set forth above. Thereafter, the vertical string is moved upwardly and downward along any radius of the right circular cylinder until a complete examination of the surface to be interrogated has occurred. It is important to note, that where such transducers are vertically stacked, alignment of the probes with respect to the centerline of the cylinder being examined can occur; the predictability of the sound path for interrogation and receipt of the interrogating radiation is readily ascertainable from the point of incidence on the cylinder parallel to center line of the cylinder being interrogated.

Unfortunately, in examination and repair of right circular structures such as control rod drive housings and the so-called stub tubes to which such housing are fastened, overhead clearance can be impaired. This is especially true where the control rod drive housing and its supporting stub tube are being repaired or replaced within a flooded nuclear reactor.

When use of the vertical string of transducers is not permitted, the design of the probe to have the requisite angles of incidence to the surface of the right circular cylinder become other than trivial. This angle includes the interaction of Snell's law with both the orientation to, separation from, and offset of the interrogating transducer with respect to the particular curvature of the cylindrical surface being interrogated.

Accordingly, it is the purpose of this invention to set forth an especially designed ultra sound transducers which can rapidly and efficiently interrogate a right circular cylinder at a point of required non destructive inspection having limited vertical overhead clearance.

SUMMARY OF THE INVENTION

An especially designed probe carries preferably five transducers for the examination of a right circular cylinder having limited vertical clearance from the point of required non destructive inspection. The probe includes a generally disc shaped body having a minimal vertical dimension and a radius slightly less than the radius of the right circular cylinder to be inspected. Insertion of the probe interior of the right circular cylinder occurs. At the periphery of the disc, there are disposed five interrogating acoustical transducers. These transducers are spaced from preselected staggered circumferential locations with respect to the right circular cylinder for examination of the water flooded cylinder with refracted rays. The respective transducers are disposed with disclosed angularities and spatial orientation from their point of intended inspection to satisfy Snell's law for both so-called "L" and "S" waves—these waves having differing speeds in the material interrogated. A process of interrogation is disclosed which includes mounting the disc on a rotatable shaft, and elevating the disc on the shaft to an elevation having the point of required interrogation intersecting the disc. Rotation of the disc then occurs with each of the interrogating transducers rotating sequentially to the point of required acoustical interrogation for the desired non destructive acoustical interrogation of the right circular cylinder.

DESCRIPTION OF THE PREFERRED EMBODIMENT

Figure 1:
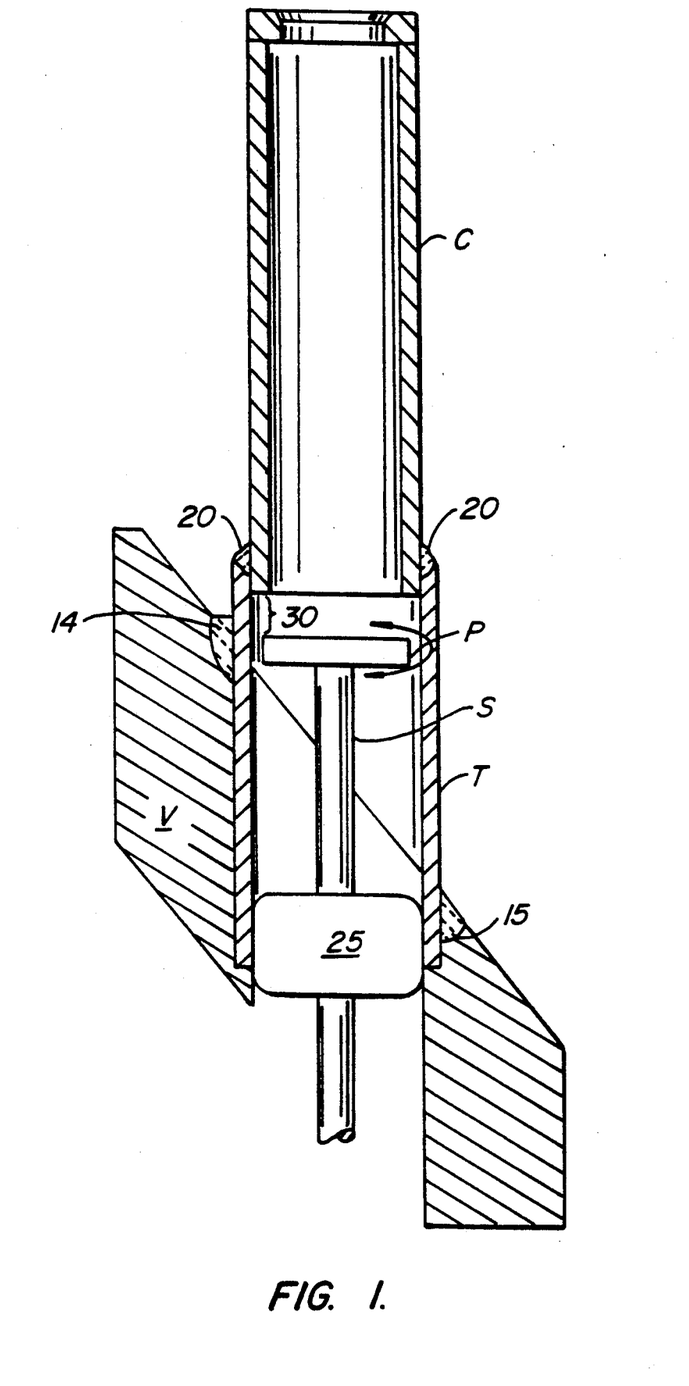
FIG. 1 is a side elevation section of a portion of a boiling water nuclear reactor illustrating a section of the reactor during a repair procedure where the point of required non destructive inspection is a stub tube at a location defining limited vertical clearance with respect to a partially removed control rod drive housing.

Referring to FIG. 1, the bottom portion of the pressure vessel of a boiling water nuclear reactor is illustrated. A section of the vessel wall is shown. A stub tube is attached by welds 14, 15 to the vessel wall.

The illustrated reactor is under repair. Specifically, as part of the repair procedure, control rod drive housing C has been cut off immediately below weld 20, extending between the top of the stub tube T and the control rod housing.

At this juncture of the repair, a situation is illustrated in which stub tube T must be inspected to ascertain whether its connection to vessel V secured by stub tube welds 14, 15 is sufficient. Otherwise further repair procedures may be required.

In the repair procedure herein undertaken, that portion of the control rod drive housing C below stub tube welds 20 has been cut away. This leaves for exposure the stub tube T and the welds 14, 15 by which the stub tube is fastened.

In the view here illustrated, a combination ultra sonic scanner positioner probe centering device and water coupling seal 25 has been installed in the bottom of the stub tube. A shaft S and probe P of this disclosure are utilized.

Stopping here, two observations can be made.

First, and between probe P and the bottom of the control rod drive housing C, a short vertical interval 30 exists. Accordingly, if ultra sound transducers are going to be intimate to the wall of the stub tube T, their disposition in a vertical string cannot occur.

Secondly, presuming that the stub tube weld 15 immediate water coupling seal 25 has to occur, again vertical clearance is extremely limited. Therefore, disposition of a series of interrogating transducers in a vertical string is not possible.

Figure 2:
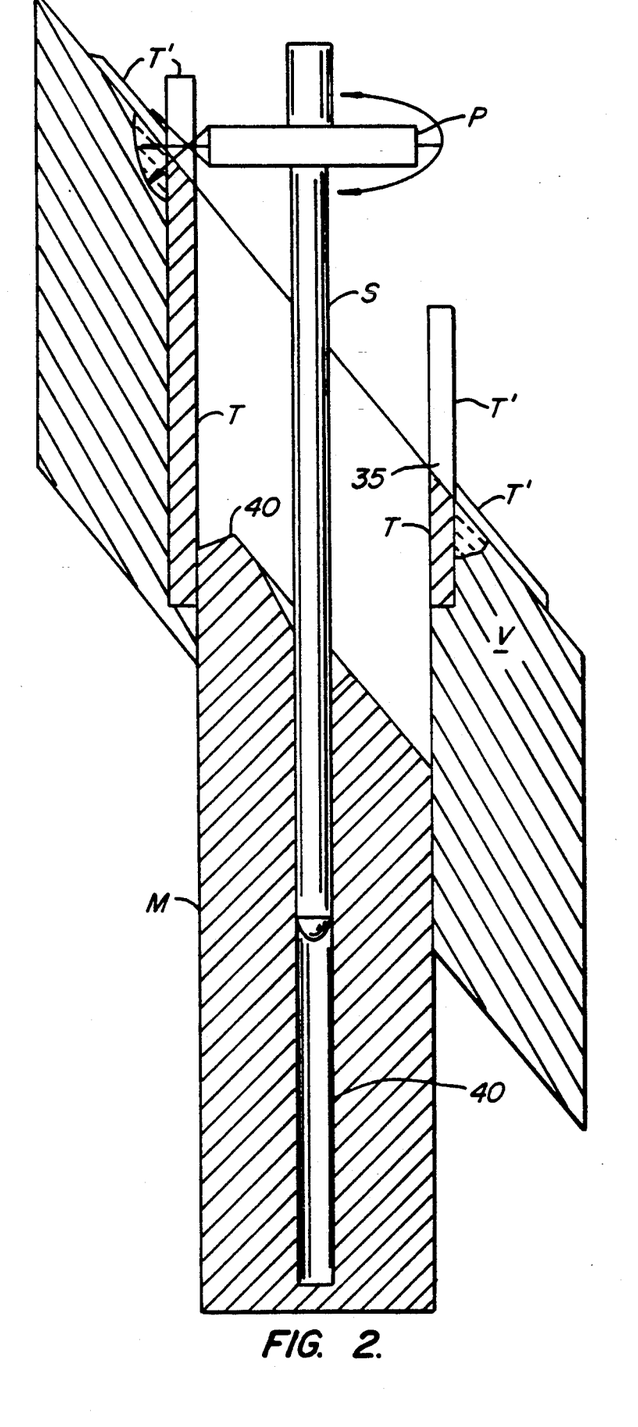
FIG. 2 is a side elevation of a similar portion of a boiling water nuclear reactor illustrating a section of the reactor during a similar repair procedure where the point of required non destructive inspection is at a location defining limited vertical clearance with respect to a partially replaced stub tube.

Referring to FIG. 2, a similar phenomenon is illustrated. In FIG. 2, the repair of the stub tube T has been required. Consequently, stub tube T has only been left in place within the vessel. At other locations beyond the vessel surface, the stub tube T has been cut away. For replacement of the stub tube, weld material buildup has been used. Specifically, at portions T', weld buildup has been utilized to construct a new stub tube structure.

The bottom of the reactor has been plugged with a sealing mandril M having a centering probe 40. Mandril M receives a shaft S which shaft S has the probe P of this invention fastened thereto. It is the function of probe P to inspect through stub tube T' formed by the buildup of weldment.

Referring to weld material forming new stub tube T, in the position of deposited weld material 35, the reader will understand that again vertical clearance is limited. This limitation of vertical clearance is especially critical with respect to the upper portion of sealing mandril M at 40. Accordingly, it is the purpose of this invention to disclose an inspecting probe P which probe P can effect the required close examination.

Figure 3:
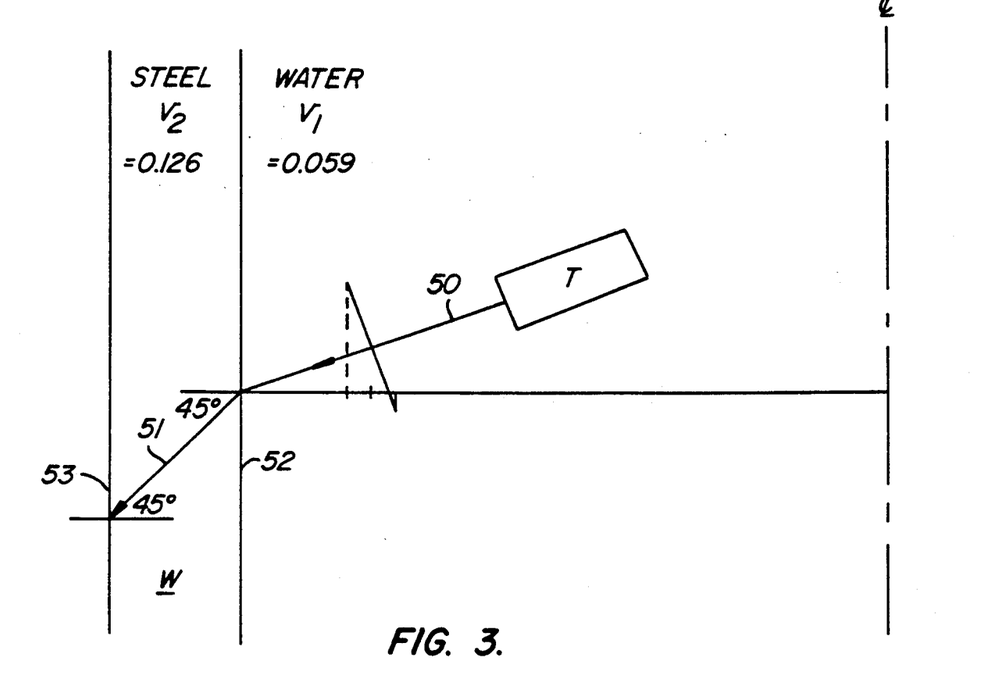
FIG. 3 is a side elevation illustrating ultra sound incidence on a planar surface with refraction with in the surface underlying the material in accordance with Snell's law.

Referring to FIG. 3, the simple case of incidence of sound along an axis 50 to interrogate a steel wall W at a 45° angle, is illustrated. Assuming that the sound is transmitted through a water couplant along axis 50, at an angle of approximately 19°, it will be refracted in accordance with the principles of Snell's law, at an angle of 45° within wall W. It will be incident upon near wall 52 and be reflected from far wall 53. The example here given is for an "S" wave.

The reader will of course realize that with the use of interrogating ultra sound, it is common to have the transducer emitting sound the same as the transducer which receives the sound. This being the case, sound will return along path 51 from either the final dimension of the wall W being tested, or alternatively, from a flaw. In such return, it will again be refracted in accordance with Snell's law, along axis 50 to the original transducer T emitting the sound.

Presuming that all transducers T could be vertically arrayed, one over another, and presuming that sound was incident to a point that is coincident with radius of the material to be interrogated at surface 52, a vertical string could be utilized. However, where vertical clearance is not present, the respective transducers utilized must be radially aligned.

Figure 4:
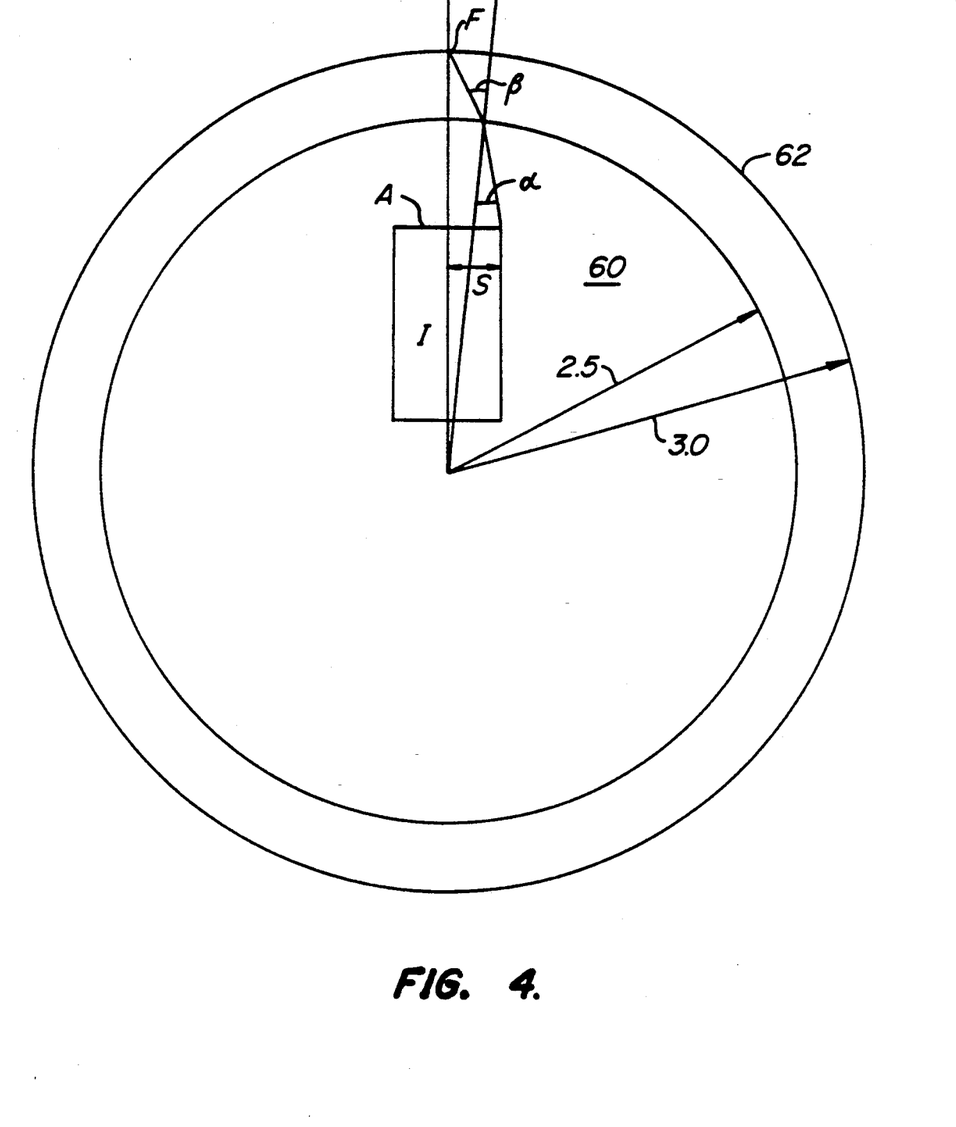
FIG. 4 illustrates a transducer offset with respect to an interrogating acoustical beam illustrating the preferable focus of the interrogating beam with respect to the back wall of a right circular structure.

Referring to FIG. 4, an exemplary calculation is utilized. A control rod drive housing B is illustrated. It has an inner radius of 2.5" and an outer radius of 3". A transducer T in the flooded state is shown. It has a defraction limited aperture A, which aperture A emits ultra sound at a first angle $\alpha$ within the water media 60 flooding the control rod drive housing C. The sound is refracted along an angle $\beta$ in accordance with Snell's law. This sound comes to a focus F and the outside diameter 52 of the cylinder.

It will be understood that the aperture A of the transducer is defraction limited. In order to approximate the focus F of the defraction limited aperture, calculations based on geometric optics are utilized. The reader will understand that these are approximations which, in testing of an actual transducer with respect to a mock up assembly, have proved sufficiently reliable to be utilized as a primary base for design considerations.

Presuming that such interrogating rays are utilized, calculations for so-called L-waves and S-waves interrogating the structure of this control rod drive housing C, can both be derived in formula as well as specific examples given. The specific derivation of the formulae is as follows:

I. RAY OFFSET EFFECT ON REFRACTED ANGLE $\alpha_i$: Incident angle at pipe I.D. surface
$\beta_L$: Refracted L-wave angle in steel
$\beta_S$: Refracted S-wave angle in steel
$V_1$: Sound velocity in water = 0.059 in/$\mu$s
$V_{2L}$: L-wave Sound velocity in steel = 0.232 in/$\mu$s
$V_{2S}$: S-wave Sound velocity in steel = 0.126 in/$\mu$s
$S$: Ray offset from the center of transducer
$r$: Pipe I.D Radius
$R$: Pipe O.D. Radius
$\alpha_{i1}$: First critical angle
$\alpha_{i2}$: Second critical angle $$\therefore \sin\alpha_i = \frac{S}{r}, \quad \frac{\sin\beta_L}{\sin\alpha_i} = \frac{V_{2L}}{V_1}, \quad \frac{\sin\beta_S}{\sin\alpha_i} = \frac{V_{2S}}{V_1}$$

$$\therefore \sin\beta_L = \frac{V_{2L}}{V_1}\sin\alpha_i = \frac{V_{2L}}{V_1} \times \frac{S}{r}, \quad \beta_L = \sin^{-1}\left(\frac{V_{2L}}{V_1} \times \frac{S}{r}\right)$$

$$\therefore \sin\beta_S = \frac{V_{2S}}{V_1}\sin\alpha_i = \frac{V_{2S}}{V_1} \times \frac{S}{r}, \quad \beta_S = \sin^{-1}\left(\frac{V_{2S}}{V_1} \times \frac{S}{r}\right)$$

$\therefore$ The greater offset $S$, the larger refracted angle $\beta_L$ or $\beta_S$.
$\therefore$ The value of ( ) must $\leq 1$ By way of example, when the inside radius equals 2.5", calculations may be made for the various angles and transducer offsets with respect to the wall as follows:

CALCULATION EXAMPLE $\therefore$ When $r = 2.5"$

Figure 5:
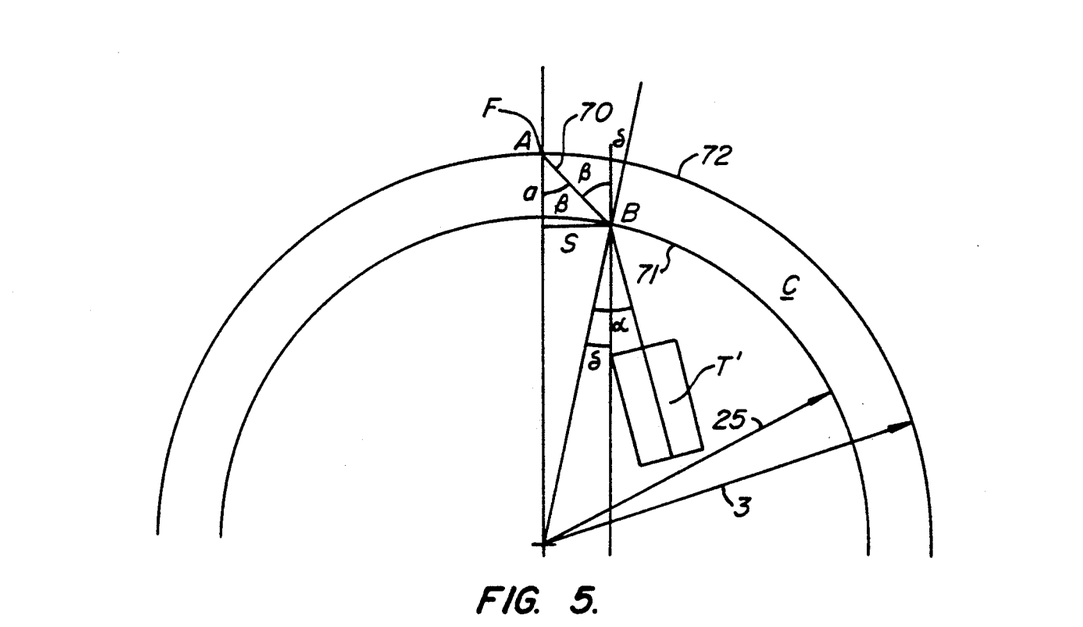
FIG. 5 illustrates the more complicated location of an acoustical head with respect to the periphery of a disc for interrogation of the material of the right circular cylinder at a preferred 45° left and right angle with respect to a plane normal to the axis of the cylinder being non destructively examined; and, FIGS. 6A and 6B are respective top plan and side elevations of the transducer head in accordance with this invention.

For L-wave, $S \leq \frac{V_1}{V_{2L}} \times r = \frac{0.059}{0.232} \times 2.5" = 0.64"$ $\alpha_{i1} = \sin^{-1}\frac{S}{r} = \sin^{-1}\frac{0.64"}{2.5"} = 14.8°$ For S-wave, $S \leq \frac{V_1}{V_{2S}} \times r = \frac{0.059}{0.126} \times 2.5" = 1.17"$ $\alpha_{i2} = \sin^{-1}\frac{S}{r} = \sin^{-1}\frac{1.17"}{2.5"} = 27.9°$ Referring to FIG. 5, the case of calculation for a control rod drive housing by a transducer T', is illustrated. In this case, the offset of the transducer T' has been based upon that offset illustrated in FIG. 4. Here, however, it is desired to have the interrogating waves 70 focus at a focus F on the outside diameter of the control rod drive housing at 72. In order to attain this focus, it is necessary to calculate both the angle of the transducer T' with respect to the inside side wall 71 of the control rod drive housing as well as offsets from the point of incidence. It is therefore necessary to compute the incident angle compensation for the circumferential scan.

Interrogation can be readily understood.
Where $\beta$: desired beam angle (for example: 45° or 60°) at a designated point "A" on pipe O.D surface.

$\alpha$: required incident angle at point "B" on pipe I.D surface to produce the desired angel $\beta$ at point "A" on O.D surface.

$\beta + 67$: actual refracted angle in steel at I. D surface.

$\alpha - \delta$. "skew angle" from the line paraller to the centerline "OA" at point "B".

$S$: ray offset at point "B" from the centerline "OA".
$R$: pipe O.D radius
$r$: pipe I.D radius
$v_r$: sound velocity in water = 0.059 in/$\mu$s.
$v_{2L}$: L-wave sound velocity in steel = 0.232 in/$\mu$s.
$v_{2S}$: S-wave sound velocity in steel = 0.125 in/$\mu$s.

By substituting $\beta$, R, r, $v_1$, $v_{2L}$ or $v_{2S}$ with known numeral in the above equations, the transducer offset (S) and it's actual required incident angle ($\alpha$) or the "skew angle" ($\alpha - \delta$) can be determined.
then:

II. INCIDENT ANGLE COMPENSATION FOR CIRCUMFERENTIAL SCAN $\because S^2 + (R - a)^2 = r^2, a = S \cdot \cot\beta$
$\therefore S^2 + (R - S \cdot \cot\beta)^2 = r^2$
$S^2 + R^2 - 2RS \cdot \cot\beta + S^2 \cdot \cot^2\beta = r^2$
$S^2(1 + \cot^2\beta) - 2RS \cdot \cot\beta + (R^2 - r^2) = 0$ $$S = \frac{2R \cdot \cot\beta \pm \sqrt{4R^2 \cdot \cot^2\beta - 4 \cdot (1 + \cot^2\beta) \times (R^2 - r^2)}}{2 \times (1 + \cot^2\beta)}$$

$$= \frac{R \cdot \cot\beta \pm \sqrt{R^2 \cdot \cot^2\beta - (1 + \cot^2\beta) \times (R^2 - r^2)}}{(1 + \cot^2\beta)}$$

$$\therefore \frac{S}{r} = \frac{\frac{R}{r}\cot\beta \pm \sqrt{\frac{R^2}{r^2} \cdot \cot^2\beta - (1 + \cot^2\beta) \times \left(\frac{R^2}{r^2} - 1\right)}}{(1 + \cot^2\beta)}$$

$$\therefore \frac{\sin\alpha}{\sin(\beta + \delta)} = \frac{V_1}{V_2};$$

$$\therefore \sin\delta = \frac{S}{r} =$$

$$\frac{\frac{R}{r}\cot\beta \pm \sqrt{\frac{R^2}{r^2} \cdot \cot^2\beta - (1 + \cot^2\beta) \times \left(\frac{R^2}{r^2} - 1\right)}}{(1 + \cot^2\beta)}$$

$$\therefore \sin\alpha = \frac{V_1}{V_2} \times \sin(\beta + \delta) =$$

$$\frac{V_1}{V_2} \times (\sin\beta \cdot \cos\delta + \cos\beta \cdot \sin\delta)$$

By way of example, where a sample calculation can be made. Where the outside radius of control rod drive housing C is 3", and the inside radius is 2.5", and 45° of incidence is desired at the outside wall 22 of the control rod drive housing C, calculations for both the angle and offset may be made as follows:

CALCULATION EXAMPLE

If $R = 3.0$ in, $r = 2.5$ in, $\beta = 45°$ at point "$A$".
$V_1 = 0.059$ in/$\mu$s  $V_{2S} = 0.126$ in/$\mu$s Then $\cot\beta = \cot 45° = 1$  $\therefore 1 + \cot\beta = 2$,
$1 + \cot^2\beta = 2$, $\frac{R}{r} = \frac{3}{2.5} = 1.2$ $\therefore \sin\delta = \frac{S}{r} =$ $$= \frac{\frac{R}{r}\cot\beta \pm \sqrt{\frac{R^2}{r^2}\cdot\cot^2\beta - (1 + \cot^2\beta) \times \left(\frac{R^2}{r^2} - 1\right)}}{(1 + \cot^2\beta)}$$

$$= \frac{1.2 \pm \sqrt{1.2^2 - 2 \times (1.44 - 1)}}{2} = \frac{1.2 \pm \sqrt{1.44 - 0.88}}{2}$$

$$= \frac{1.2 \pm 0.748}{2} = \begin{cases} 0.974 \text{ for}(+\text{sign}) \\ 0.226 \text{ for}(-\text{sign}) \end{cases}$$

$$\therefore \delta = \begin{cases} 76.9° \text{ for}(+\text{sign}) \\ 13.1° \text{ for}(-\text{sign}) \end{cases}$$

$\therefore$ For(+sign)  $\sin\alpha = \frac{V_1}{V_{2S}} \times \sin(45° + \delta) =$ $\frac{0.059}{0.126} \times (45° + 76.9°) = 0.468 \times 0.849 = 0.397$ $\therefore \alpha = 23.4°$ $\therefore$ For(−sign)  $\sin\alpha = \frac{V_1}{V_{2S}} \times \sin(45° + \delta) =$ $\frac{0.059}{0.126} \times (45° + 13.1°) = 0.468 \times 0.849 = 0.397$ $\therefore \alpha = 23.4°$ same result as for + sign.
$\therefore \alpha - \delta = 23.4° - 13.1° = 10.3°$
$\therefore S = r \times \sin\delta = 2.5$ in $\times \sin 13.1° = 2.5$ in $\times 0.227 = 0.567$ in
Due to the physical restriction, the + sign resulting $\delta = 76.9°$ and $(\alpha - \delta) = -53.5°$, $S = 2.43$ in should be ignored.

Figures 6A, 6B:
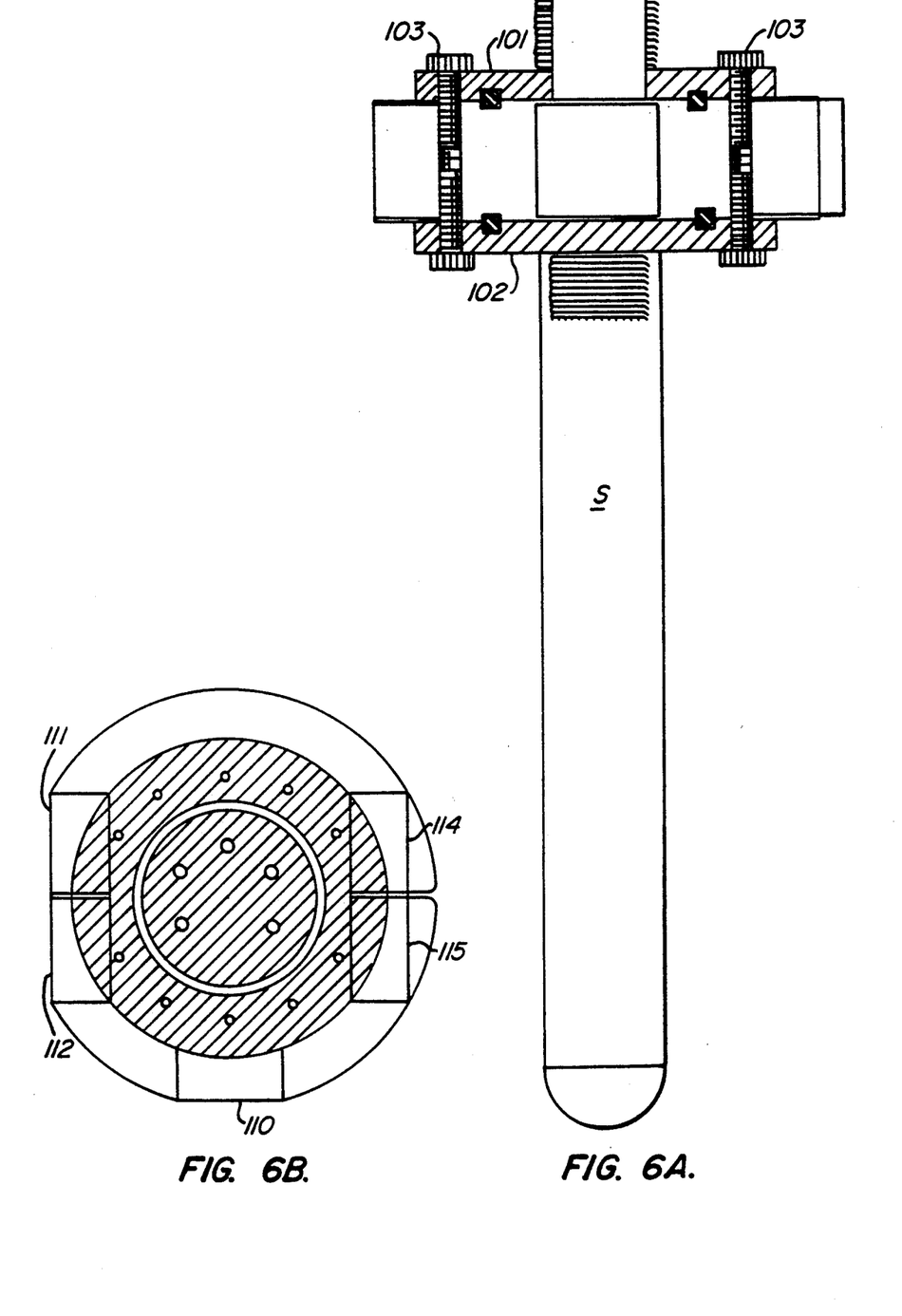

Referring to FIGS. 6A and 6B, the sample construction of a probe in accordance with this invention can be understood. A shaft S is utilized, having an upper plate 101 and a lower plate 102, connected by cross bolts 103. Five transducers are utilized. A first straight ahead transducer 112 is utilized. Second and third transducers 111 and 112 are utilized for looking at a 45° angle upwardly, and a 45° angle downwardly.

The calculation of these respective transducers can occur in accordance with that of FIG. 3.

The respective looking left and looking right transducers 114 and 115 are a far more complicated problem, and are illustrated with respect to FIG. 5. Specifically, and depending upon whether they look right or left, these respective transducers must be positioned towards and away from the wall of the control rod drive housing C which they are interrogating. Further, the transducers must be offset and oriented as offset in that angulation required for the refraction of the sound to and from the material being analyzed. It should be noted that for both S waves and L waves of interrogation, the angles will change.

In the practical embodiment of this invention, it has been required that the depth of the probe between plates 101 and 102 not exceed "1".

Once the parameters are known, defraction limited lenses with respect to the transducers T can be selected from standard designs.

The reader will understand that as a simplification, geometric optics have been utilized. These geometric optics are substituted in situations where an acoustical aperture is defraction limited. That is to say, the ratio of the wave length of the aperture through which the waves pass, and the actual dimension of the aperture, are close to one. Accordingly, and although it has been found that the calculations herein utilized are generally useful for the probe design, it is required that an actual test of the transducers with respect to a mockup occur.

It will be further understood, that where the particular dimensions being inspected change, the design of probe P will have to change in accordance with the dimensions of the cylinder being interrogated. For example, we contemplate four specific probes following the design parameters set forth herein. Examples of those probes are first probes which inspect the existing stub tube to reactor pressure vessel well. Additionally and secondly, a specially designed probe is utilized where weld buildup material is inspected. Thirdly, weld buildup material forming the bridge to the new stub tube weld requires a different dimension probe. Finally, a probe especially designed for inspecting the new stub tube to new control rod drive housing weld is utilized.

The reader will understand that in this design I prefer the use of "S" waves to examine the stub tube and control rod drive housing because of their higher resolving power. I prefer that these waves have the preferred 45° interrogative angles in the inspected materials. It will be understood that different material types, thicknesses and geometric configurations could require different waves. For example a porous cylinder may be more beneficially inspected with "L" waves because of their superior penetration power.

It can thus be seen that the disclosed features are exemplary within the limitations set forth herein.

What is claimed is:

1. In the acoustical ultra sound examination of a right circular cylinder flooded with an acoustical coupling fluid having at least a point of required acoustical examination with limited vertical clearance, a probe for conducting said required acoustical examination and means for mounting said probe comprising:
   a generally disc shaped body, said body having a minimum vertical dimension restricted to contain a series of outwardly generally radially disposed acoustical transducers, said body having a radial dimension less than the radial dimension of said cylinder to enable penetration of said disc shaped body into the interior of said right circular cylinder to be acoustically interrogated;
   means mounting said generally disc shaped body for elevation and rotation with respect to the axis of said right circular cylinder to be interrogated;
   at least five interrogating acoustical transducers disposed on the periphery of said disc shaped body including transducers having interrogating acoustical orientations with respect to said right circular cylinder to enable respective interrogations of said point of said right circular cylinder through said acoustical coupling fluid and thereafter within said right circular cylinder to be interrogated at respective angularly up, angularly down, angularly left, angularly right, and substantial normal orientations whereby said right circular cylinder can be elevated and rotated for the sequential inspection by said transducers of a required point of interrogation interior of said right circular cylinder.

2. The invention of claim 1 and wherein said acoustical coupling fluid flooding said right circular cylinder is water.

3. A process for the acoustical ultra sound examination of a right circular cylinder flooded with an acoustical coupling fluid having at least a point of required acoustical examination with limited vertical clearance with respect to said point, said process comprising the steps of:

providing a generally disc shaped body, said body having a minimum vertical dimension restricted to contain a series of outwardly generally radially disposed acoustical transducers at differing circumferential locations on the periphery of said body, said body having a radial dimension less than the radial dimension of said right circular cylinder to enable penetration of said disc shaped body into the interior of said right circular cylinder to be acoustically interrogated;

mounting said generally disc shaped body for elevation and rotation with respect to the axis of said right circular cylinder to be interrogated;

providing at least five interrogating acoustical transducers disposed on the periphery of said disc shaped body including transducers having angular acoustical interrogating orientations with respect to said right circular cylinder to enable respective interrogations from said right circular cylinder at respective angularly up, angularly down, angularly left, angularly right, and normal orientations;

elevating said disc shaped body to the elevation in said right circular cylinder having said point of required inspection;

rotating said body to sequentially register said transducers at said point of required acoustical interrogation for the sequential ultra sound examination from said point at said required respective angularly up, angularly down, angularly left, angularly right, and normal orientations.

4. The process of claim 3 and including the step of flooding said right circular cylinder with water.

* * * * *